US008651305B1

(12) United States Patent
Lunn

(10) Patent No.: US 8,651,305 B1
(45) Date of Patent: Feb. 18, 2014

(54) RECLOSABLE CONTAINER CLOSURE

(75) Inventor: Melanie M. Lunn, Brookings, SD (US)

(73) Assignee: Simplified Dosing Incorporated, Brookings, SD (US)

( * ) Notice: Subject to any disclaimer, the term of this patent is extended or adjusted under 35 U.S.C. 154(b) by 752 days.

(21) Appl. No.: 12/570,478

(22) Filed: Sep. 30, 2009

(51) Int. Cl.
*B65D 41/20* (2006.01)
*A61M 5/32* (2006.01)

(52) U.S. Cl.
USPC ........... 215/244; 215/247; 215/228; 215/237; 604/415

(58) Field of Classification Search
USPC ................. 215/209, 237, 245, 260, 247, 249; 222/494, 546, 556; 604/415
See application file for complete search history.

(56) References Cited

U.S. PATENT DOCUMENTS 3,970,121 A 7/1976 Brandt
4,175,597 A 11/1979 Peterson
4,326,569 A 4/1982 Vaillancourt
4,469,151 A 9/1984 Wilson
5,897,033 A * 4/1999 Okawa et al. ................. 222/212
5,931,828 A * 8/1999 Durkee ......................... 604/403
6,866,164 B2 * 3/2005 Branson et al. .......... 222/153.14
2002/0035820 A1 3/2002 Farris
2002/0130139 A1 * 9/2002 Shiraishi et al. .............. 222/105
2002/0139088 A1 10/2002 Woodworth
2007/0051426 A1 3/2007 Harman
2007/0079894 A1 4/2007 Kraus
2008/0283143 A1 11/2008 McKibbin
2009/0107948 A1 * 4/2009 Brand et al. .................. 215/247

* cited by examiner

*Primary Examiner* — Anthony Stashick
*Assistant Examiner* — James N Smalley
(74) *Attorney, Agent, or Firm* — Jeffrey A. Proehl; Woods, Fuller, Shultz & Smith, P.C.

(57) ABSTRACT

A closure assembly for mounting on a container includes a base configured for mounting on the container and defining an aperture through which the interior of the container is accessible. The base comprises a perimeter, a separator mounted on and extending across the perimeter with the aperture being formed in the separator, and a valve positioned on the separator. The valve extends across the aperture in the separator, and is openable by the application of pressure on the valve and self-closable upon removal of the pressure from the valve. The assembly also includes a cover for selectively covering the aperture. The cover is mounted on the base and is movable with respect to the base between a closed position and an open position. The closed position is characterized by the aperture not being accessible and the open position is characterized by the aperture being accessible.

20 Claims, 5 Drawing Sheets

RECLOSABLE CONTAINER CLOSURE

BACKGROUND

1. Field

The present disclosure relates to medicine containers and more particularly pertains to a new reclosable container closure for a container permitting repeated accesses to the contents of the container with a syringe, and particularly with a syringe designed for oral administration of a medicine.

2. Description of the Prior Art

Containers are often used to contain medicinal liquids for administration to a person. For example, a container may be used to hold a quantity of a medicine that is to be orally administered to a young child using an oral syringe. Typical practice in such a situation is to remove the cap from the container body and then withdraw the liquid from the container using an oral syringe; however, this operation can be difficult as the user attempts to withdraw the accurate dose while holding the syringe, while not spilling the contents from the bottle. Additionally, even the simple matter of keeping track of the cap can also be challenging when attempting to perform these tasks for an ill and unhappy child,

SUMMARY

In view of the foregoing, the present disclosure describes a new reclosable closure for a container which may be utilized for permitting repeated accesses to the contents of the container with an oral syringe in a highly convenient and simple manner.

The present disclosure relates to a closure assembly for mounting on a container for controlling access to contents in the interior of the container. The closure assembly comprises a base configured for mounting on the container. The base defines an aperture through which the interior of the container is accessible when the base is mounted on the container. The base comprises a perimeter, and a separator mounted on and extending across the perimeter, with the aperture being formed in the separator. The base also comprises a valve positioned on the separator. The valve extends across the aperture in the separator. The valve is openable by the application of pressure on the valve, and self-closable upon removal of the pressure from the valve. The assembly further includes a cover for selectively covering the aperture. The cover is mounted on the base, and is movable with respect to the base between a closed position and an open position. The closed position is characterized by the aperture not being accessible and the open position is characterized by the aperture being accessible.

In another aspect, the disclosure relates to a reclosable container system that comprises a container body having an interior for receiving a fluid, an opening into the interior, and a mouth portion having the opening formed therein. The system comprises a closure assembly mounted on the mouth portion of the container body for controlling access to contents in the interior of the container body through the opening. The closure assembly comprises a base mounted on the container. The base defines an aperture through which the interior of the container is accessible when the base is mounted on the container. The base comprises a perimeter, a separator mounted on and extending across the perimeter with the aperture being formed in the separator, and a valve positioned on the separator. The valve extends across the aperture in the separator. The valve is openable by the application of pressure on the valve and self-closable upon removal of the pressure from the valve. The system further comprises a cover for selectively covering the aperture, the cover being mounted on the base. The cover is movable with respect to the base between a closed position and an open position, with the closed position being characterized by the aperture not being accessible and the open position being characterized by the aperture being accessible.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

Figure 1:
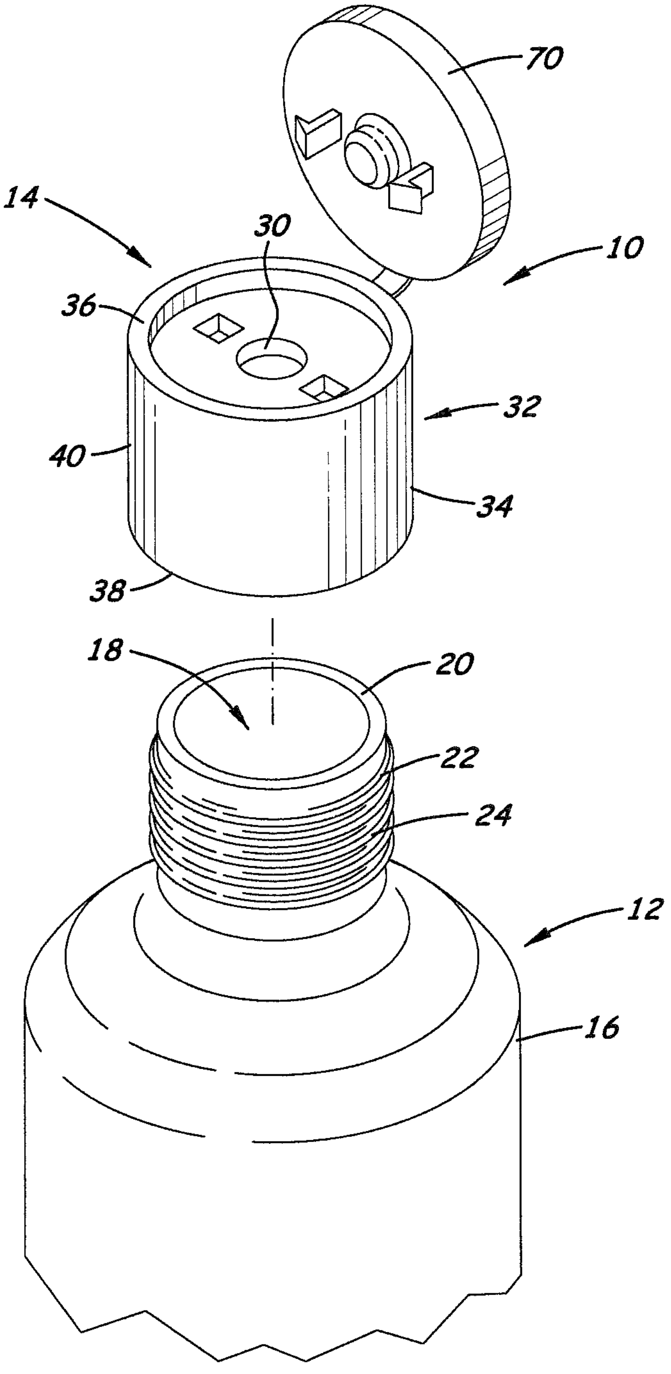
FIG. 1 is a schematic perspective exploded view of a new reclosable closure system including a container and a closure assembly according to the present disclosure.
Figure 2:
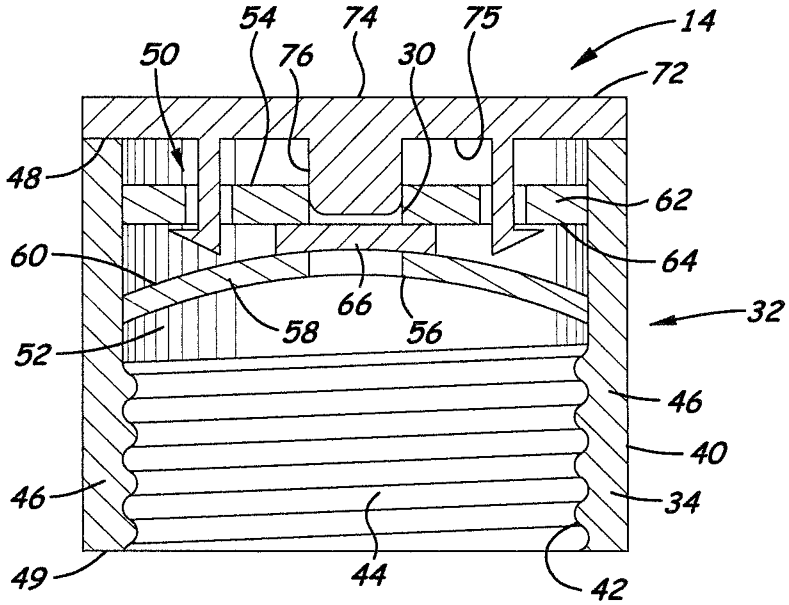
FIG. 2 is a schematic side sectional view of the closure assembly, according to an illustrative embodiment, showing the cover in a closed position.
Figure 3:
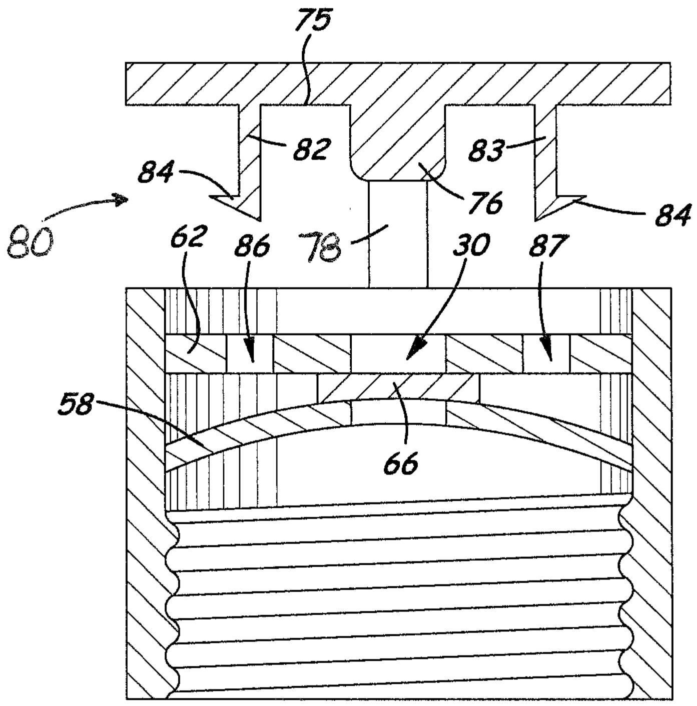
FIG. 3 is a schematic side sectional view of the closure assembly, according to an illustrative embodiment, showing the cover in an open position.
Figure 4:
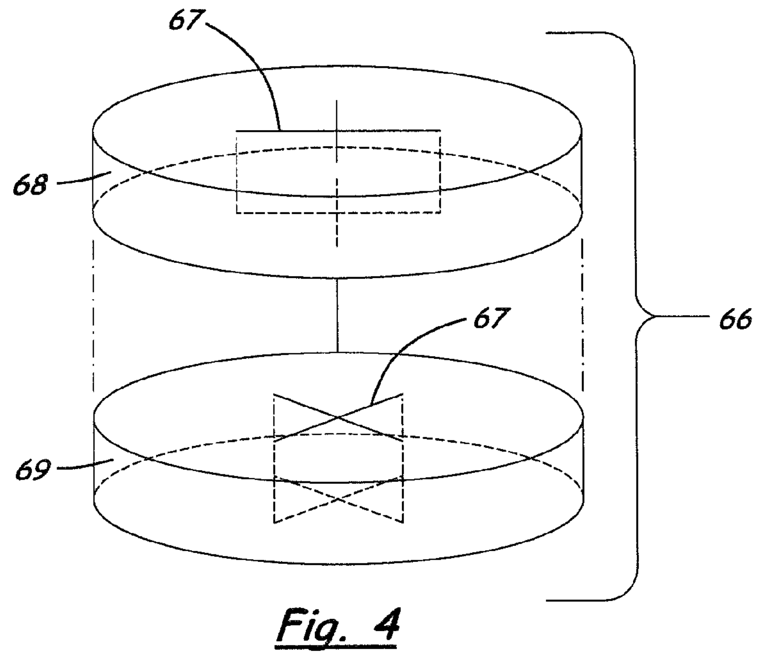
FIG. 4 is a schematic perspective exploded view of an illustrative valve embodiment shown removed from the base of the closure assembly.
Figure 5:
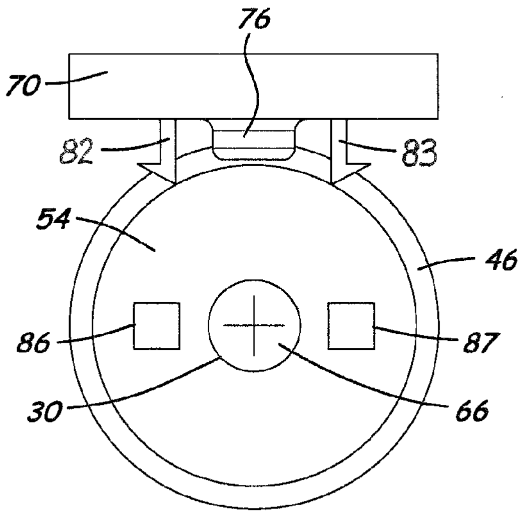
FIG. 5 is a schematic top view of the closure assembly, according to an illustrative embodiment.
Figure 6:
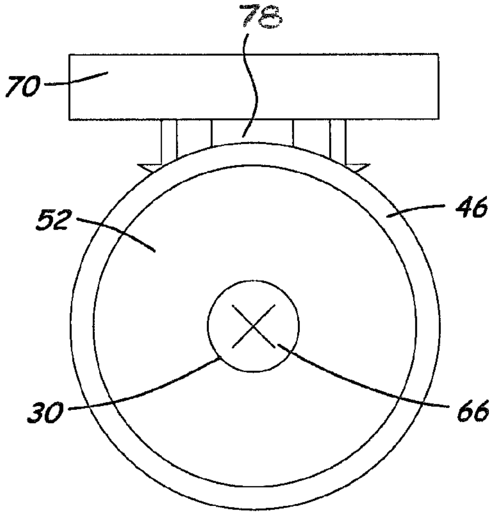
FIG. 6 is a schematic bottom view of the closure assembly, according to an illustrative embodiment.
Figure 7:
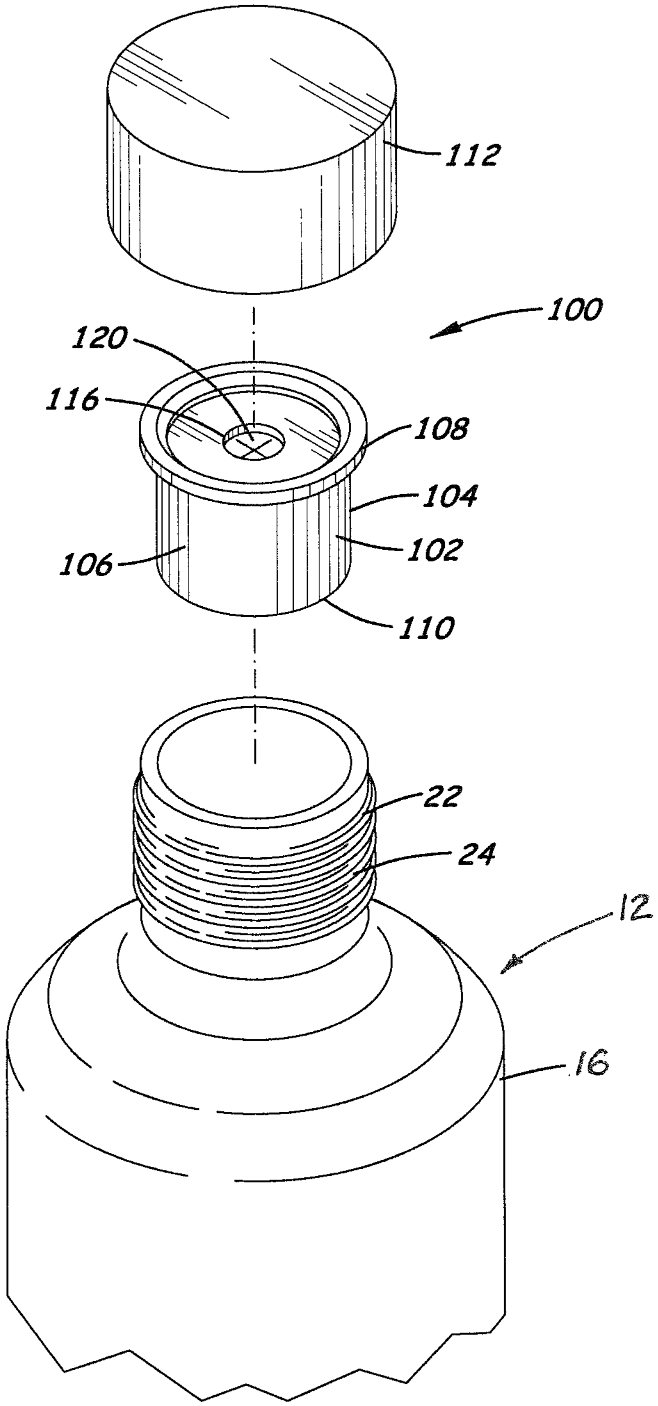
FIG. 7 is a schematic perspective exploded view of an optional embodiment of the new reclosable closure system including a container and a closure assembly.
Figure 8:
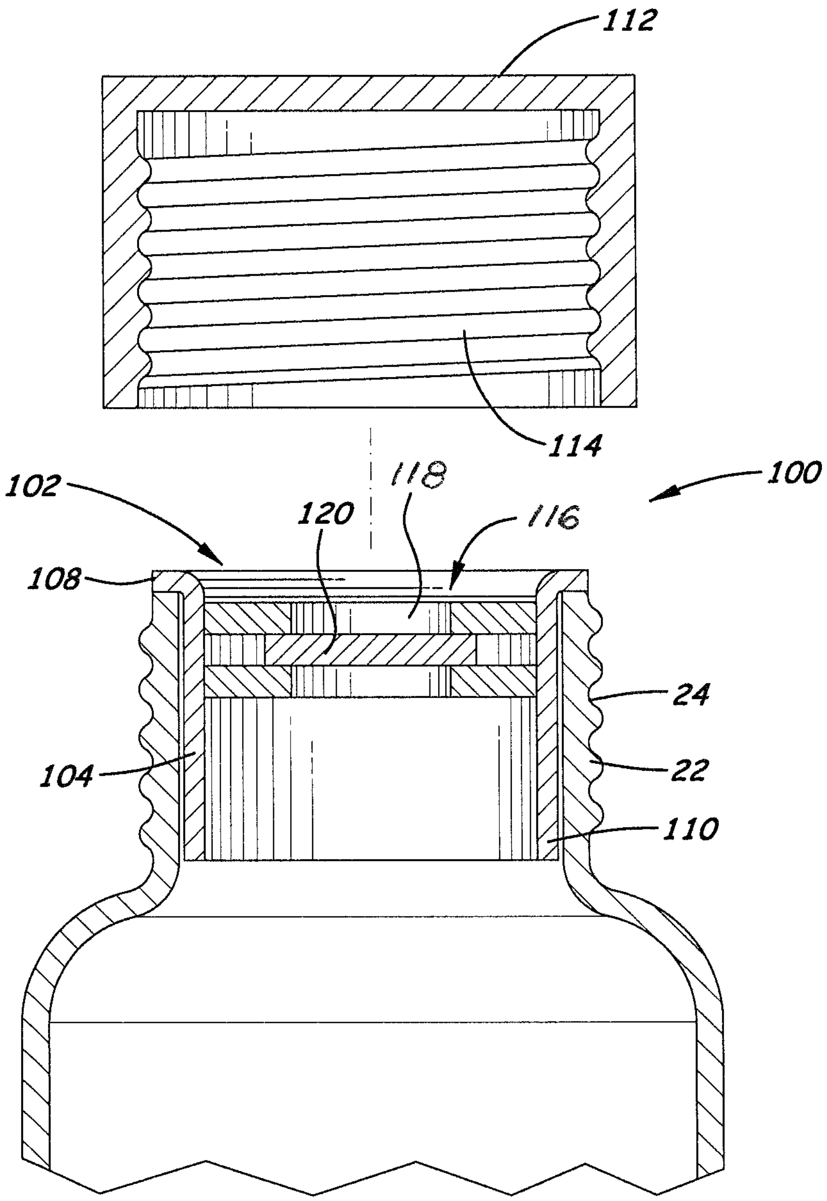
FIG. 8 is a schematic side sectional view of the optional embodiment of the closure assembly shown in FIG. 7.

With reference now to the drawings, and in particular to FIGS. 1 through 8 thereof, a new reclosable container closure for a container embodying the principles and concepts of the disclosed subject matter will be described.

One aspect of the disclosure relates to a reclosable container system 10 that broadly includes a container 12 and a closure assembly 14 for the container. The disclosure also relates to aspects of the closure assembly 14 apart from the container.

In greater detail, the container 12 of the system 10 may include a container body 16 that has an interior 18 for receiving a fluid, such as a medicinal solution, although the container may be used to hold other types of liquids. The container body 16 has an opening 20 into the interior, and may include a mouth portion 22 that forms the opening 20. An outer surface 24 of the mouth portion 22 may have a plurality of exterior threads formed thereon for removable attachment of the closure assembly 14, although other removable and non-removable types of attachment may be utilized for attaching the closure system to the container. One optional configuration will be described below.

The closure assembly 14 may thus be removably mounted on the container 12 in the manner that permits separation of the closure assembly and container without damage or destruction to the closure assembly or container, may be more permanently mounted on the container 12 such that separation requires damage or destruction to the container or closure assembly. The closure assembly 14 may define an aperture 30 through which contents of the interior 18 of the container body is accessible.

The closure assembly 14 may comprise a base 32 that is mounted (either removably or more permanently) on the container 12. The base 32 may include a perimeter 34 with a top 36 and a bottom 38. The perimeter 34 may also have an outer surface 40 and an inner surface 42. A portion of the inner surface 42 of the perimeter may have a plurality of interior threads 44 formed thereon for engaging the exterior threads of the mouth portion 22 of the container. In the illustrative embodiments in the drawings, the perimeter 34 comprises a perimeter wall 46 having an upper edge 48 and a lower edge 49.

The base 32 may further comprise a separator 50 which may have the aperture 30 formed therein. The separator 50 may have an inner face 52 that is directed toward the interior 18 of the container body 16, and an outer face 54 that is directed outwardly from the interior 18, and the aperture may extend from the inner face to the outer face. The aperture 30 may thus be formed by a channel with some degree of length. The inner face 52 may be substantially concave in shape, although that is not critical. The aperture 30 may be positioned at the peak 56 of the concave inner face 52. The outer face 54 may be substantially planar in shape, although again the shape is not critical to the function. In the illustrative embodiments, the separator 50 may comprise a first separator wall 58 that extends across the perimeter 34, and may be joined to the perimeter along a perimeter region 60 of the first separator wall, and may form the concave inner face 52 of the separator 50. The illustrative separator 50 may further comprise a second separator wall 62 that extends across the perimeter 34. The second separator wall 62 may be joined to the perimeter 34 along a perimeter region 64 of the second separator wall, and may form the outer face 54 of the separator 50.

The base 32 may also include a valve 66 that is positioned on the separator 50 and may extend across the aperture 30 in the separator. In some preferred embodiment, the valve 66 may be opened by the application of pressure on the surface of the valve 66, such as by the pressing or pushing of a pointed object, such as the end of an oral syringe utilized for the oral administration of medicines. The valve 66 may be self-closable upon removal of the pressure from the valve, so that, for example, when the tip of the syringe is withdrawn from the valve, the opening closes and the contents of the container is resisted from passing through the valve. The valve 66 may have any suitable construction for this purpose, and illustratively comprises one, and optionally two, flexible and resilient membranes 68, 69 with small slits 67 formed therein that may be opened by the application of a narrow object to the membrane adjacent to the slit. In some embodiments, a pair of membranes 68, 69 overlap with the respective slits oriented so that the slits cross each other but do not align with each other except at the intersection. In some embodiments, the slit in each membrane has an "X-shaped" configuration, and these X-shaped slits may also be out of alignment so that they do not register with each other (although may intersect), but the sections of the membrane formed by the slits are able to be deflected away from each other to create an opening when force is applied to the sections of flexible membrane. This configuration of the valve is illustrative, and variations of this configuration, as well as other configurations, may be employed.

The closure assembly 14 may further have a cover 70 for selectively covering the aperture 30. The cover 70 may be mounted on the base 32, and may be movable with respect to the base between a closed position in which the aperture is not accessible and an open position in which the aperture is accessible. The cover may have many different but suitable configuration for serving the purpose of covering the aperture, and the covers described herein are to be considered illustrative but not limiting of the types of covers that may be devised for use. The cover 70 may be mounted on the perimeter 34 of the base, and may be pivotable with respect to the perimeter through a pivotable mounting on the perimeter. The cover 70 has a perimeter region 72, and a portion of the perimeter region may be mounted to the perimeter wall. The pivotable mounting may be provided in any suitable manner, such as by a hinge, and in the illustrative embodiments the connection is provided by a living hinge 78 formed of a flexible web of material connecting the cover 70 to the perimeter 34. The cover 70 may also be characterized by having a top side 74 and a bottom side 75.

The cover 70 may have a plug structure 76 for providing some degree of fluid tightness to the closure assembly in addition to the valve 66 when the cover is in the closed position. The plug structure 76 may be located on the bottom side of the cover 70 to extend outwardly from the bottom side, so that the plug structure may be partially inserted into the aperture 30 in the separator 50 when the cover is closed. The plug structure 76 may be an integral portion of the same part that forms the cover, or may be a part that is attached to the part or parts that forms the cover.

The closure assembly 14 may further include a locking structure 80 that is configured to releasably lock the cover 70 in the closed position. The locking structure may take various suitable, forms, and these forms may or may not be "childproof". In the illustrative embodiments, the locking structure 80 includes at least one, and preferably a pair of, tabs 82, 83 that extend from the cover 70 to engage the base 32 when the cover is in the closed position and to resist, but not prevent, movement of the cover from the closed to the open position. The tabs 82, 83 may be positioned on the bottom side 75 of the cover 70 to extend toward the separator 50 when the cover 70 is in the closed position. The tabs 82, 83 may also have a hook 84 located adjacent to a free end of the tab for engaging the separator, as will be described in greater detail below.

The locking structure 80 may also include at least one, and preferably a pair of, openings 86, 87 formed on the separator

50. The openings 86, 87 of the pair may be located on opposite sides of the aperture 30, and each tab of the pair of tabs may be suitably aligned with one of the openings when the cover 70 is in the closed position such that the tabs are inserted into the openings when the cover is in the closed position. The openings 86, 87 may be located on the separator 50 such that the hook 84 on each tab engages an edge of the separator about the respective openings when the tabs 82, 83 are inserted into the openings. In the illustrative embodiments, the opening 86, 87 are formed in the second separator wall 62 of the separator.

In some embodiments, the base 32 of the closure assembly is configured and constructed such that application of a pinching force to the base releases the hooks 84 of the tabs from the edge of the respective openings 86, 87. Application of the pinching force to the outer surface 40 of the perimeter 34 distorts the second separator wall 62 and causes the openings to move with respect to the hooks on the tabs so that the tabs and hooks are able to move out of the respective openings without being blocked by the edge of the openings.

In an optional embodiment of the closure assembly, indicated by the reference number 100, the base 102 has a perimeter 104 that is designed to be inserted into the interior of the mouth portion 22, of the container body 16. The perimeter 104 may have an outer surface 106 that is configured for insertion into an interior of the mouth portion 22 of the container, and in some embodiments the outer surface is substantially smooth and cylindrical, although other configurations may be employed. The perimeter 104 may include a positioning lip 108, and the positioning lip may extend outwardly from the perimeter wall 110 of the perimeter. The positioning lip 108 may be positioned at a top of the perimeter wall 110. The positioning lip 108 may prevent the base from being inserted too far into the mouth portion 22 of the container body 16, so that the base does not move past the interior of the mouth portion and move into the interior of the main portion of the container body 16. A cover 112 may be configured fit over the mouth portion 22 of the container body, and may be configured with interior threads 114 to engage exterior threads located on an outer surface 24 of the mouth portion 22 of the container, although other means for removably mounting the cover 112 on the container may be employed. The cover 112 may be free of any connection to the perimeter 104 such that the cover 112 is freely rotatable with respect to the container 12 and the base 102. In other embodiments, the cover 112 may be connected to the base 102 in the manner described above or using other structures.

The closure assembly 100 may also include any of the elements described in connection with the closure assembly 10, and may thus include a separator 116 that is mounted on and extends across the perimeter 104. An aperture 118 may be formed in the separator 116. A valve 120 may be positioned on the separator 116, and may extend across the aperture 118 in the separator. The valve may be a single valve, or comprise an assembly of two or more valves.

In use, the user of the system 10 is able to access the contents of the container, such as a medicinal fluid to be administered orally to a young child using an oral syringe, by means of the closure assembly 14, while being able to reclose the closure assembly after the access to the fluid so that the contents of the container 12 may be repeatedly accessed and a dose dispensed until the container is empty. The cover 70 of the closure assembly may be opened to expose and gain access to the aperture 30. In some embodiments, opening the cover 70 involves pinching opposite sides of the perimeter 34 of the base 32 toward each other to release the tabs 82, 83 from the edges of the openings 86, 87 in the base. The container system may be inverted to bring the contents of the interior 18 of the container body 16 toward the closure assembly and the aperture 30. The tip or end of a syringe, such as an oral syringe, may be inserted into the valve 66 of the closure assembly so that the tip of the syringe passes through the valve 66 and is surrounded by the contents of the container. Fluid may then be withdrawn from the container into the syringe, and the tip of the syringe is withdrawn from the valve and the aperture when a desired amount is drawn into the syringe. The container system may then be brought right side up, and the cover moved from the open position to the closed position until the next withdrawal of fluid is desired.

It should be appreciated from the foregoing description that, except when mutually exclusive, the features of the various embodiments described herein may be combined with features of other embodiments as desired while remaining within the intended scope of the disclosure.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A reclosable container system comprising:

a container body having an interior for receiving a fluid, the container body having an opening into the interior and a mouth portion having the opening formed therein; and a closure assembly mounted on the mouth portion of the container body for controlling access to contents in the interior of the container body through the opening, the closure assembly comprising:

- a base mounted on the container, the base defining an aperture through which the interior of the container is accessible when the base is mounted on the container, the base comprising:
  - a perimeter;
  - a separator mounted on and extending across the perimeter, the aperture being formed in the separator; and
  - a valve positioned on the separator, the valve extending across the aperture in the separator, the valve comprising a preformed opening being openable to dispense contents from the container by the application of mechanical pressure on an exterior the valve, the preformed opening of the valve being self-closable upon removal of the pressure from the valve; and
- a cover for selectively covering the aperture, the cover being mounted on the base, the cover being movable with respect to the base between a closed position and an open position, the closed position being characterized by the aperture being inaccessible and the cover not contacting the valve so that the valve is closed when the cover is in the closed position, the open position being characterized by the aperture being accessible.

2. The container system of claim 1 wherein the cover is pivotally mounted on the perimeter.

3. The container system of claim 1 wherein the cover includes a plug structure configured to partially insert into the aperture in the separator when the cover is in the closed position and be withdrawn from the aperture when the cover is moved into the open position.

4. The container system of claim 1 additionally comprising a locking structure configured to releasably lock the cover in a closed position.

5. The container system of claim 4 wherein the locking structure comprises:

at least one tab extending from the cover, the at least one tab having a hook located adjacent to a free end of the tab; and at least one opening formed on the separator in alignment with the at least one tab when the cover is in the closed position such that the tab is inserted into the opening, the at least one opening being located on the separator such that the hook engages an edge of the separator about the opening when the at least one tab is inserted into the opening.

6. The container system of claim 5 wherein the at least one opening comprises a pair of openings on the separator, the pair of openings being located on opposite sides of the aperture, and wherein the at least one tab comprises a pair of tabs extending from the cover, each tab of the pair of tabs being aligned with one of the openings of the pair of openings.

7. The container system of claim 5 wherein the base is configured such that application of a pinching force to the base releases the hook of the at least one tab from the edge of the at least one opening.

8. The container system of claim 1 wherein the separator comprises:

a first separator wall extending across the perimeter and having a perimeter region joined to the perimeter, the first separator wall forming an inner face of the separator oriented toward the interior of the container body; and a second separator wall extending across the perimeter and having a perimeter region joined to the perimeter, the second separator wall forming an outer face of the separator.

9. A closure assembly for mounting on a container for controlling access to contents in the interior of the container, the closure assembly comprising:

a base configured for mounting on the container, the base defining an aperture through which the interior of the container is accessible when the base is mounted on the container, the base comprising:

a perimeter;

a separator mounted on and extending across the perimeter, the aperture being formed in the separator; and a valve positioned on the separator, the valve including a membrane extending across the aperture in the separator, the valve comprising a preformed slit in the membrane being openable to dispense contents from the container by the application of pressure to the valve by mechanical contact with an outer surface of the valve, the preformed slit in the membrane of the valve being self-closable upon removal of the pressure from the valve;

wherein the base is configured so that an end of an oral syringe is insertable into the base and contactable with the outer surface of the membrane of the valve to apply mechanical contact pressure to the valve to open the valve;

a cover mounted on the base and being movable with respect to the base between a closed position and an open position, the closed position being characterized by the aperture being inaccessible for contacting the outer surface of the valve so that the valve remains closed when the cover is in the closed position, the open position being characterized by the aperture being accessible to permit the application of pressure by mechanical contact to the valve.

10. The closure assembly of claim 9 wherein the cover is pivotally mounted on the perimeter.

11. The closure assembly of claim 9 additionally comprising a locking structure configured to releasably lock the cover in a closed position.

12. The closure assembly of claim 11 wherein the locking structure comprises:

at least one tab extending from the cover, the at least one tab having a hook located adjacent to a free end of the tab; and at least one opening formed on the separator in alignment with the at least one tab when the cover is in the closed position such that the tab is inserted into the opening, the at least one opening being located on the separator such that the hook engages an edge of the separator about the opening when the at least one tab is inserted into the opening, the at least one opening being formed in the second separator wall of the separator.

13. The closure assembly of claim 12 wherein the at least one opening comprises a pair of openings on the separator, the pair of openings being located on opposite sides of the aperture, and wherein the at least one tab comprises a pair of tabs extending from the cover, each tab of the pair of tabs being aligned with one of the openings of the pair of openings.

14. The closure assembly of claim 12 wherein the base is configured such that application of a pinching force to the base releases the hook of the at least one tab from the edge of the at least one opening.

15. A reclosable container system comprising:

a container body having an interior for receiving a fluid, the container body having an opening into the interior and a mouth portion having the opening formed therein; and a closure assembly mounted on the mouth portion of the container body for controlling access to contents in the interior of the container body through the opening, the closure assembly comprising:

a base mounted on the container, the base defining an aperture through which the interior of the container is accessible when the base is mounted on the container, the base comprising:

a perimeter;

a separator mounted on and extending across the perimeter, the aperture being formed in the separator; and a valve positioned on the separator, the valve including a pair of membranes extending across the aperture in the separator, the valve including a preformed slit in each of the membranes, said slits being oriented in an intersecting relationship such that the slits are openable to dispense contents from the container by the application of pressure to the valve by mechanical contact with an outer surface of the valve, the valve being self-closable upon removal of the pressure from the valve;

wherein the base is configured so that an end of an oral syringe is insertable into the base and contactable with the outer surface of the valve to apply mechanical contact pressure to the valve and open the valve such that the end of the oral syringe enters the interior of the container for access to any fluid in the interior; and a cover mounted on the base and being movable with respect to the base between a closed position and an open position, the closed position being characterized by the aperture being inaccessible for contacting the outer surface of the valve so that the valve remains closed when the cover is in the closed position, the open position being characterized by the aperture being accessible to permit the application of pressure by mechanical contact to the valve.

16. The closure assembly of claim 9 wherein the base is open above the valve when the cover is in the open position to expose the outer surface of the valve to contact by the end of a syringe inserted into the base.

17. The container system of claim 1 wherein the valve includes a preformed opening therethrough.

18. The container system of claim 17 wherein the valve includes a membrane, and the preformed opening extends through the membrane.

19. The container system of claim 18 wherein the preformed opening is formed by a slit extending through the membrane.

20. The container system of claim 18 wherein the valve includes a pair of overlapping membranes, and the preformed opening is formed by a slit in each membrane with the slits being oriented in an intersecting relationship.

* * * * *